(12) United States Patent
Kim et al.

(10) Patent No.: US 12,276,612 B2
(45) Date of Patent: Apr. 15, 2025

(54) ACTIVE ILLUMINATION-BASED MULTISPECTRAL CONTAMINATION SANITATION INSPECTION SYSTEM

(71) Applicants: The United States of America, as Represented by the Secretary of Agriculture, Washington, DC (US); SafetySpect Inc., Sherman Oaks, CA (US)

(72) Inventors: Moon S Kim, Ashton, MD (US); Jianwei Qin, Ellicott City, MD (US); Diane E Chan, Odenton, MD (US); Lyndel Meinhardt, College Park, MD (US); Insuck Baek, Burtonsville, MD (US); Kenneth Barton, Palm City, FL (US); Fartash Vasefi, Sherman Oaks, CA (US)

(73) Assignees: The United States of America, as Represented by the Secretary of Agriculture, Washington, DC (US); SafetySpect Inc., Sherman Oaks, CA (US)

( * ) Notice: Subject to any disclaimer, the term of this patent is extended or adjusted under 35 U.S.C. 154(b) by 169 days.

(21) Appl. No.: 17/529,019

(22) Filed: Nov. 17, 2021

(65) Prior Publication Data
US 2023/0152232 A1    May 18, 2023

(51) Int. Cl.
*G01N 21/64* (2006.01)
*A61L 2/10* (2006.01)
(Continued)

(52) U.S. Cl.
CPC ............ *G01N 21/6486* (2013.01); *A61L 2/10* (2013.01); *A61L 2/28* (2013.01); *G01N 21/94* (2013.01)

(58) Field of Classification Search
CPC .... G01N 21/6486; G01N 21/94; G01N 21/31; G01N 2021/3181; G01N 2201/0221;
(Continued)

(56) References Cited

U.S. PATENT DOCUMENTS 5,159,398 A * 10/1992 Maekawa .......... G01N 15/1427
356/417
5,208,651 A * 5/1993 Buican ................. G01J 3/4406
356/451
(Continued)

FOREIGN PATENT DOCUMENTS

WO    2020148726 A1    7/2020

OTHER PUBLICATIONS

ISR/WO (International Search Report/Written Opinion) in International Application No. PCT/US2022/049831 dated Mar. 8, 2023.
(Continued)

*Primary Examiner* — Mohamed K Amara
(74) *Attorney, Agent, or Firm* — John Fado; Matthew Bussan

(57) ABSTRACT

The contamination sanitation inspection system (CSIS) allows a user to capture an image of a large scene (such as a food processing line, a food service facility, a food products storage area, or a plant production area/facility) and identify contamination within the scene and preferably represent the contamination on a spatially accurate map (or floorplan) so that contamination within the inspection map area is clearly identified and recorded for subsequent treatment. In an alternative embodiment, the CSIS also includes a decontamination system to sanitize any identified contamination.

25 Claims, 5 Drawing Sheets
(1 of 5 Drawing Sheet(s) Filed in Color)

(51) Int. Cl.
*A61L 2/28* (2006.01)
*G01N 21/94* (2006.01)

(58) Field of Classification Search
CPC .............. G01N 2201/0616; G01N 2201/0627; G01N 2201/0696; G01N 21/6456; A61L 2/10; A61L 2/28
See application file for complete search history.

(56) References Cited

U.S. PATENT DOCUMENTS

| | | | |
|---|---|---|---|
| 5,749,830 A * | 5/1998 | Kaneko | A61B 1/0638 348/E5.038 |
| 6,587,575 B1 * | 7/2003 | Windham | A22B 5/007 382/110 |
| 7,547,508 B1 * | 6/2009 | Lefcourt | G01N 21/94 435/29 |
| 8,310,544 B2 | 11/2012 | Kim et al. | |
| 8,749,672 B2 * | 6/2014 | Komiya | H04N 25/445 348/266 |
| 9,198,578 B2 * | 12/2015 | Zuzak | G01J 3/0208 |
| 10,426,852 B2 * | 10/2019 | Dobrinsky | A61L 9/00 |
| 10,820,789 B2 * | 11/2020 | Ogata | H04N 23/74 |
| 11,154,188 B2 * | 10/2021 | Talbert | H04N 23/745 |
| 11,201,993 B1 * | 12/2021 | Wang | H04N 23/45 |
| 11,639,897 B2 * | 5/2023 | Barron | G01N 33/6839 356/317 |
| 2003/0160182 A1 | 8/2003 | Petrich et al. | |
| 2009/0153797 A1 * | 6/2009 | Allon | A61B 3/12 362/11 |
| 2009/0309960 A1 | 12/2009 | Park et al. | |
| 2011/0279679 A1 * | 11/2011 | Samuel | H04N 23/73 348/E5.085 |
| 2012/0044394 A1 * | 2/2012 | Komiya | H04N 25/135 348/E9.003 |
| 2014/0193050 A1 * | 7/2014 | Miller | G06T 5/50 382/128 |
| 2017/0142314 A1 * | 5/2017 | Moore | H04N 23/71 |
| 2017/0209050 A1 * | 7/2017 | Fengler | G01J 3/4406 |
| 2018/0234603 A1 * | 8/2018 | Moore | H04N 23/72 |
| 2020/0309702 A1 * | 10/2020 | Barron | G01N 21/6486 |
| 2021/0199590 A1 * | 7/2021 | Shashurin | G01J 3/0218 |
| 2021/0228757 A1 | 7/2021 | Vasefi et al. | |
| 2021/0356391 A1 * | 11/2021 | Stewart | G01N 21/25 |
| 2023/0277065 A1 * | 9/2023 | Islam | A61B 5/1455 433/29 |
| 2023/0363328 A1 * | 11/2023 | Lys | G01J 3/0264 |
| 2023/0375476 A1 * | 11/2023 | Vasefi | H04L 9/50 |
| 2024/0225454 A9 * | 7/2024 | Islam | A61B 5/742 |

OTHER PUBLICATIONS

"Basics of Light Microscopy & Imaging, Special Edition of Imaging & Microscopy", Olympus, 2006, 55 pages.

Petty, "Fluorescence Microscopy: Established and Emerging Methods, Experimental Strategies, and Applications in Immunology", Microscopy Research and Technique, vol. 70, 2007, pp. 687-709.

* cited by examiner

ACTIVE ILLUMINATION-BASED MULTISPECTRAL CONTAMINATION SANITATION INSPECTION SYSTEM

FIELD OF THE INVENTION

The disclosed subject matter relates to imaging systems associated with contamination and sanitation inspections. Specifically, the subject matter described herein allows a user to capture an image of a large scene (such as a food processing line facility or food products storage areas) and identify contamination within the scene and represent the contamination on a spatially accurate map (or floorplan) so that contamination within the inspection/map area is clearly identified and recorded for subsequent treatment.

BACKGROUND OF THE INVENTION

Outbreaks of food-borne illnesses (particularly bacterial illnesses) continue to be a problem in the food service industry. In many cases, bacterial contamination of food products and food handling facilities are the cause of the problem. One potential solution is an efficient and effective contamination identification system and an effective inspection protocol.

Handheld inspection devices give inspectors a degree of versatility and flexibility that improves both the speed and quality of the inspection process as well as immediate mitigation. Existing scanning technology relies primarily on the use of physical filters (and similar hardware devices) on imaging systems. There is currently no digital image chip-based sensor technology (e.g., existing CCD or CMOS image chips) designed for selecting and using specific wavebands for multispectral imaging and processing. Existing chip-based digital color image sensors are predominantly used for broadband RGB color imaging (e.g., Bayer filter array) and cannot be used for narrow-band multispectral fluorescence or reflectance imaging. The inventors have previously demonstrated that multispectral imaging can be effective to detect contamination on food materials or processing equipment (e.g., chlorophyll in animal fecal matter residues on plant crops or meat, biofilms). Examples of the currently-used technology are evident in the inventor's U.S. Pat. No. 8,310,544. More recent systems that perform some to the functions identified herein include U.S. patent application Ser. No. 17/161,567 (Pub. No. US 2021/0228757). Both U.S. Pat. No. 8,310,544 and U.S. patent application Ser. No. 17/161,567 are hereby incorporated by reference.

Sensor chip-based multispectral imaging allows for miniaturized instrumentation compared to existing technology. The system described herein incorporates orientation/position sensing capabilities and target recognition algorithms (such as a rangefinder and scene/facial/surface recognitions) that enable non-expert technicians to conduct effective inspections. For example, instead of requiring the user to precisely position an inspection device, the user simply moves the device toward a targeted surface so that multispectral imaging is automatically triggered (pulsed illumination and multiple images acquired within a second) when the device senses the surface in a certain distance range, with incorporation of a safety feature to prevent initiation of ultraviolet (UV)-based fluorescence imaging if any faces are detected within the field of view.

Use of the invention described herein could significantly facilitate image-based safety/quality inspection for food/ agricultural processing and production environments with user-friendly, automated multispectral image analysis/processing and data presentation. The United States Department of Agriculture (USDA) Environmental Microbial & Food Safety Laboratory (EMFSL) research has developed multispectral imaging techniques for contamination and sanitation inspection in part as a response to food safety issues related to the US Food and Drug Administration's Hazard-Analysis-Critical-Control-Point regulations and Food Safety Modernization Act guidelines/requirements. The technology and techniques described herein can facilitate the detection of specific contaminants of interest by making detection quicker, easier, and more intuitive in real-world user scenarios. The rapid detection helps the inspector to initiate disinfection or risk mitigation. One way of risk mitigation is to use UV germicide illumination to deactivate pathogen and remove the treat.

The system described herein also allows a user/inspector to conduct contamination inspections regardless of the lighting condition of the inspected space. This capability is important for conducting consistent and standardized inspections under a wide variety of ambient light environments. If contamination is present in the inspected space, the product of the inspection is an image of the inspected area showing the position of a fluorescent image of the contamination on a floor plan/map of the inspected space.

The need exists for an effective multispectral imaging system that allows a human inspector to capture an image of a large scene (such as a food processing line, facility, or food products storage areas) and identify contamination within the scene and represent the contamination on a user interface including on a spatially accurate map (or floorplan) so that contamination including invisible and poorly visible contaminations within the area including the map area is clearly identified and recorded for subsequent treatment and remediation. The digital report can be created to proof the cleanliness above human visual inspection capabilities. The current invention comprises a hand-held contamination sanitation inspection system (hereinafter, a "CSIS") that enables an operator to quickly conduct and document sanitation inspections of a designated facility regardless of the lighting conditions in the inspected area.

SUMMARY OF THE INVENTION

This disclosure is directed to a handheld contamination sanitation inspection system (CSIS). The CSIS comprises at least one active illumination light (preferably an LED light) and at least one multispectral camera. In the preferred embodiment, the multispectral camera comprises a chip-based multispectral camera. The CSIS further comprises a processor that controls the active illumination light and the multispectral camera.

In operation, the CSIS is structured so that as a user directs the CSIS toward a target inspection area in ambient light, the processor directs the CSIS multispectral camera to acquire a multispectral image of the inspection area in ambient light. Immediately thereafter, the processor pulses at least one active illumination light and simultaneously acquires an illuminated multispectral image of the inspection area. The processor then subtracts the ambient light multispectral image from the illuminated multispectral image to produce a multispectral fluorescence image of any contamination in the inspection area.

BRIEF DESCRIPTION OF THE DRAWINGS

The patent or application file associated with this disclosure contains at least one drawing executed in color. Copies of this patent or patent application publication with color drawing(s) will be provided by the Office upon request and payment of the necessary fee.

Note that assemblies/systems in some of the FIGS. may contain multiple examples of essentially the same component. For simplicity and clarity, only a small number of the example components may be identified with a reference number. Unless otherwise specified, other non-referenced components with essentially the same structure as the exemplary component should be considered to be identified by the same reference number as the exemplary component.

DETAILED DESCRIPTION OF PREFERRED EMBODIMENTS

System Description

Figure 1:
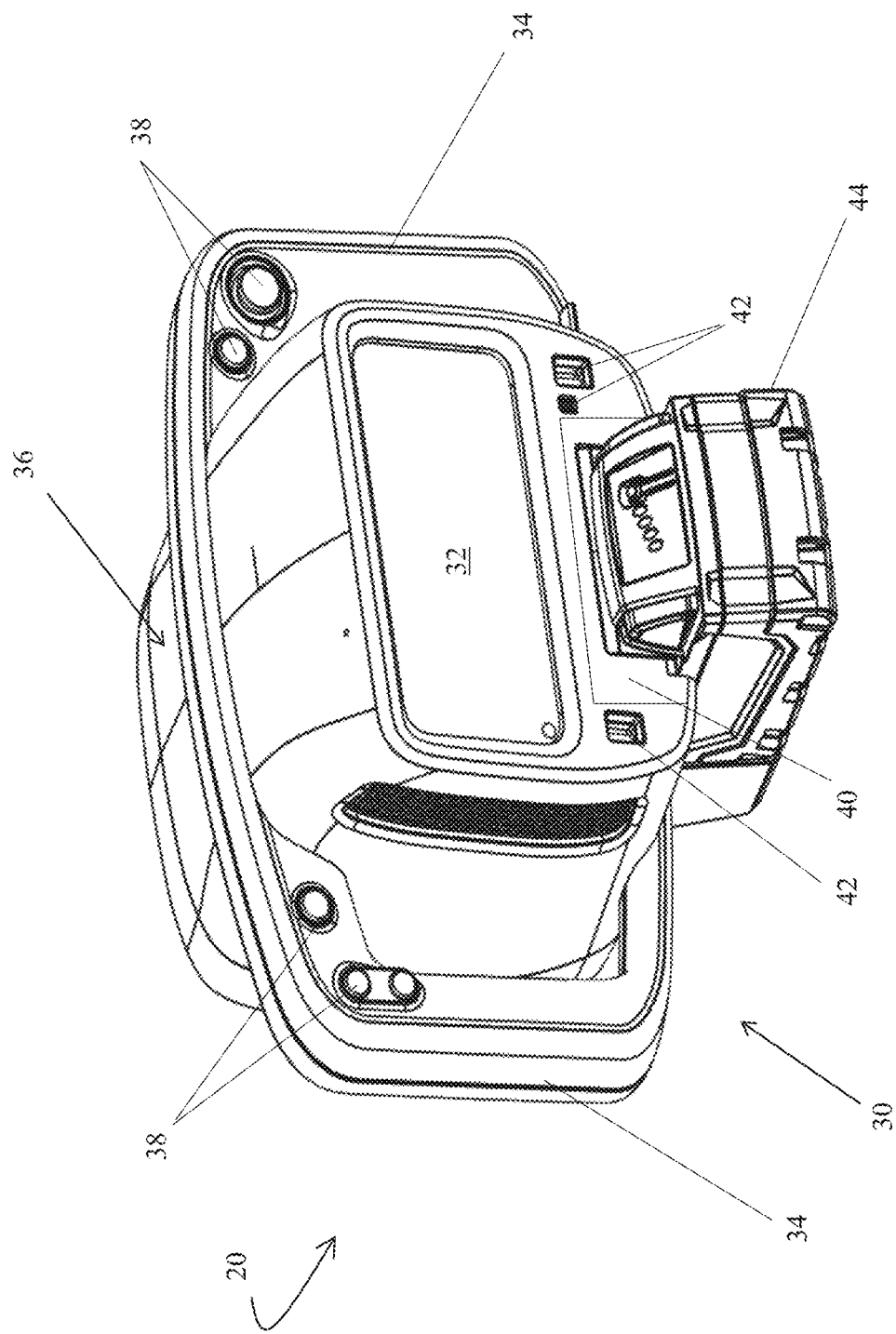
FIG. 1 is a perspective view of a user/operator-facing first side 30 of an exemplary embodiment of a CSIS 20. The user-facing first side 30 of the CSIS 20 faces toward the user during CSIS 20 operation. In the preferred embodiment, the user-facing first side 30 includes (among other things) a user interface screen 32.
Figure 2:
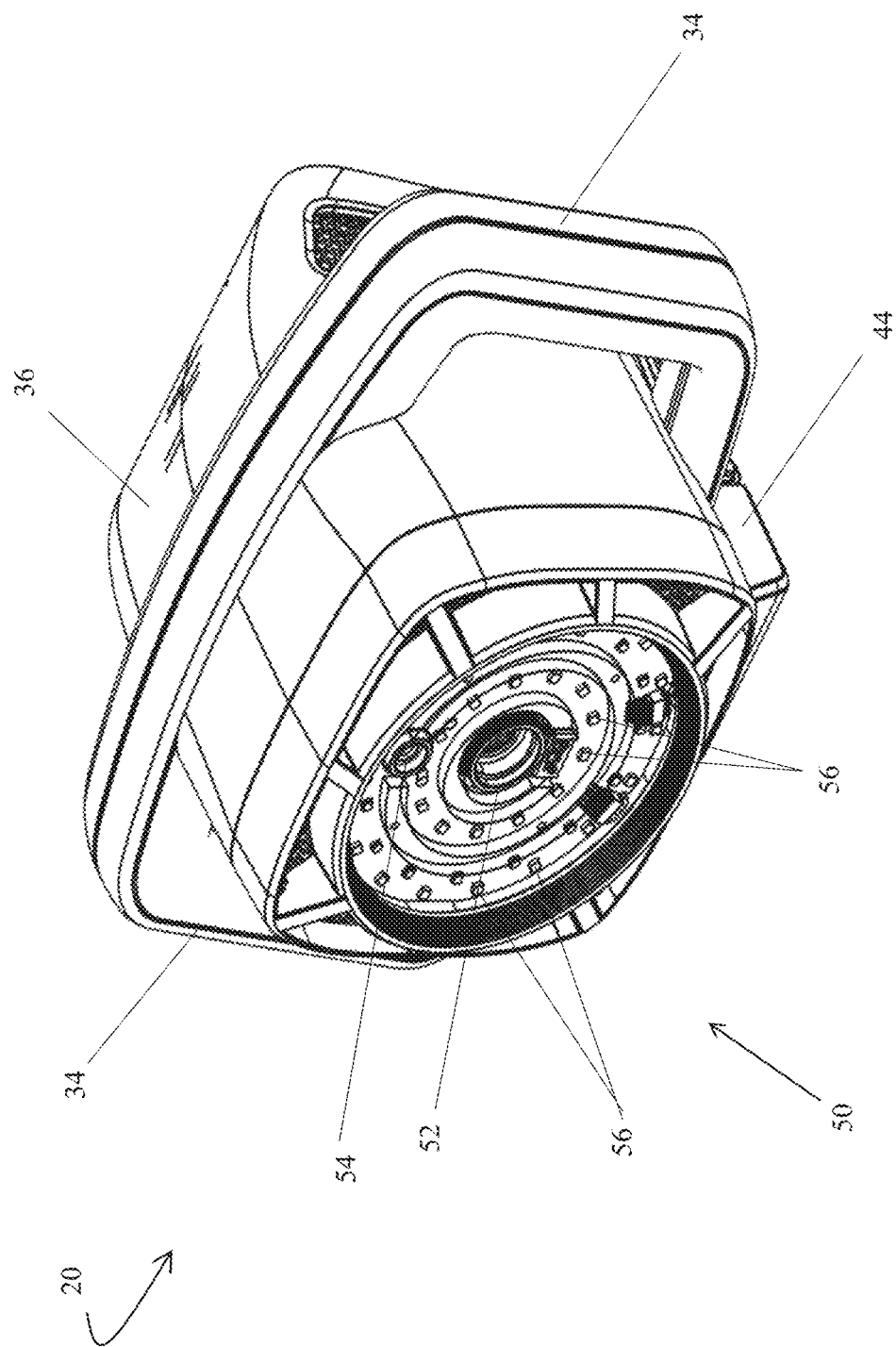
FIG. 2 is a perspective view of an inspection area-facing second side 50 of an exemplary embodiment of a CSIS 20. The inspection area-facing second side 50 is opposite the user-facing first side 30. The inspection area-facing second side 50 of the CSIS faces away from the operator and toward the inspection area during CSIS 20 operation. In the preferred embodiment, the inspection area-facing second side 50 includes (among other things) light emitting diode (LED) lights 56, and a multispectral imaging primary camera 52, and a designated UV camera 54. In the preferred embodiment, the multispectral imaging primary camera 52 comprises a chip-based multispectral camera. In alternative embodiments, the multispectral imaging primary camera 52 may comprise a conventional RGB camera with a multiband pass filter configured to produce a multispectral image.

As generally shown in FIGS. 1 and 2, the system 20 described herein comprises a contamination sanitation inspection system (hereinafter, a "CSIS") 20. The CSIS 20 enables the rapid detection of saliva, respiratory droplets, bacteria, fungi, or other organic residues that may be present in kitchens, dining areas, and food processing facilities, and other areas where food is present. The system 20 processes and records the detection data and thereby provides immediate documentation of contaminants on inspected surfaces. The CSIS 20 incorporates the technology to wirelessly communicate the inspection process, which allows remotely located personnel to provide oversight and respond to inspection issues in real time.

FIG. 1 shows an exemplary embodiment of a user-facing first side 30 of the CSIS system 20. As shown in FIG. 1, the user-facing first side 30 includes an operator interface screen 32 that, in combination with the various function activation/selection control means (i.e. buttons, switches, levers, dials, rheostats, knobs, etc.) 38, enables the user to control and communicate with the system 20. In operation, a user holds the CSIS 20 by at least one of the handles 34 and directs the main body 36 of the system 20 toward an inspection area.

The CSIS 20 is specifically designed as a hand-held device. For the purposes of this disclosure, a "handheld device" is a device fully operable and useable by a single operator. A handheld device is sized so that the handheld device is compact and light enough to be carried and maneuvered by hand by a single operator via one or more handles 34. In the preferred embodiment, the "hand grip(s)" 34 comprises an "ear" type configuration with two essentially symmetric handles. In alternative embodiments, the hand grip(s) 34 feature may comprise a single pistol-type grip or another configuration that enables a user to easily operate the system 20 with one or two hands.

The CSIS 20 may further include onscreen "touch screen" menus, or a remotely controlled wireless system for controlling the functions of the system 20 remotely. A data processor 40 is generally housed within the lower portion of the main body 36 of the CSIS 20. Various storage, communication, and utility devices may be connected to the processor 40 through access ports 42 included on the CSIS 20 main body 36. A chargeable battery module 44 is attached to the base of the system's 20 main body 36 to power the system 20. In alternative embodiments, the CSIS 20 may send and receive data to/from a remote processor 40 that is not housed within the body 36 of the CSIS.

FIG. 2 shows an inspection area-facing second side 50 of an exemplary embodiment of a CSIS 20. The inspection area-facing second side 50 is opposite the user-facing first side 30. The inspection area-facing second side 50 of the CSIS 20 faces away from the user and toward the inspection area during CSIS 20 operation. The inspection area-facing second side 50 includes a multispectral primary camera 52. In the preferred embodiment, the multispectral primary camera 52 comprises a "chip-based multispectral camera".

Figure 3:
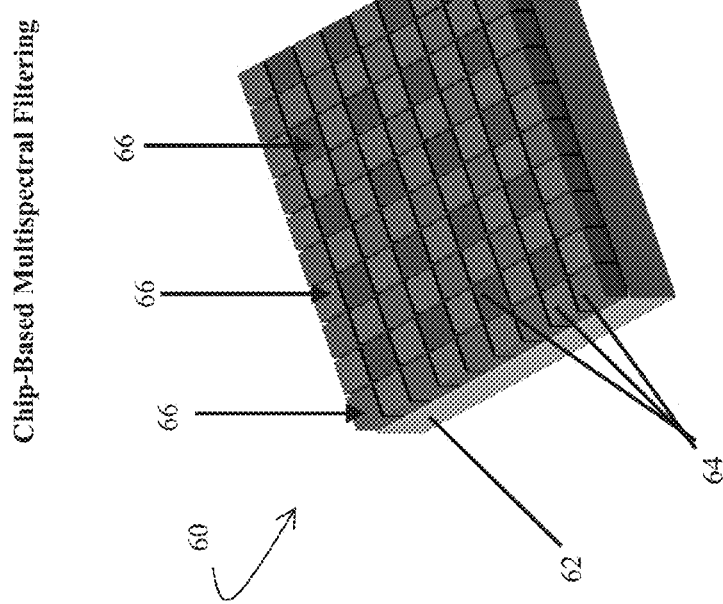
FIG. 3 shows a color elevational schematic view of a multispectral filtering chip 60 comprising an array of bandpass filters 64 positioned to filter incident light 66 reaching a photosensor 62.

For the purposes of this disclosure, a "chip-based multispectral camera" comprises a camera wherein incident light 66 passing through a camera lens is directed to a multispectral imaging chip 60 comprising a photosensor 62 covered by a matrix of narrow band pass filters 64—as best shown in FIG. 3. Although the exemplary embodiment shown in FIG. 3 depicts a relatively small bandpass filter 64 matrix, in operation, the filter 64 matrix may comprise hundreds or thousands of narrow bandpass filters 64, the number of filters 64 being proportional to the resolution of the chip-based multispectral camera. The photosensor 62 receives the filtered light and generates a "multispectral image" which is then directed to the processor 40.

Figure 4:
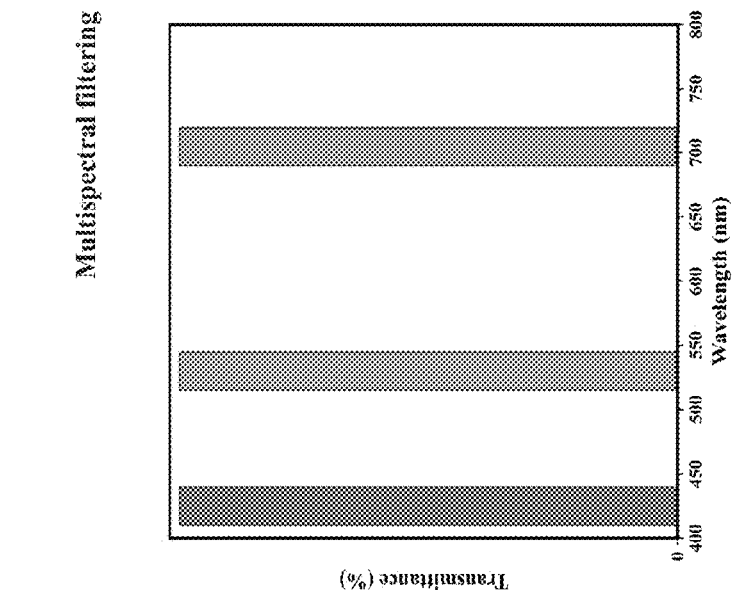
FIG. 4 is a graphical representation showing three exemplary selected wavebands that may comprise the wavebands selected to produce a multispectral image.

For the purposes of this disclosure, a "multispectral image" is an electronic image comprising two or three selected/targeted light wavebands so that all other light wavebands are filtered out, as best shown in FIG. 4. The light wavebands that comprise a "multispectral image" are selected to generate a fluorescent response from contamination within an illuminated area. As shown in FIG. 4, in the exemplary embodiment shown in FIG. 3, the three target light wavebands comprise about 420-440 nm, 520-540 nm, and 690-710 nm. In alternative embodiments, different specific wavebands may be targeted. The targeted wavebands may have a span of about 10-30 nm. Preferably the targeted wavebands have a span of about 20 nm each.

In alternative embodiments, the multispectral primary camera 52 may comprise a conventional RGB camera with supplemental/separate multiple bandpass filter hardware configured to produce a multispectral image. For the purposes of this disclosure, an "RGB camera" is defined as a visible light camera with standard broadband filters through which colored images are acquired specifically to replicate human color vision perception. As discussed supra, the CSIS 20 may also include a designated UV camera 54 with multiple band pass filters. The cameras 52, 54 are at least partially surrounded by an array of active illumination LED lights 56. In further alternative embodiments, the system may comprise more than one RGB or chip-based cameras. In any case, all cameras/imaging systems are controlled by the processor 40.

In the preferred embodiment, the multispectral imaging chip 60 is paired with an active illumination system and specialized software to enable the CSIS 20 to detect and identify contamination regardless of ambient light conditions. As shown in FIG. 2, active illumination is provided by one or more of the of the LED lights 56 on the inspection area side 50 of the CSIS 20. The LED lights 56 may comprise any lights (or combination of lights) in the electromagnetic spectrum including ultra-violet (UV) lights, near-infrared (NIR) lights, and infrared (IR) lights.

At least one pulsed light source 56 is used to provide synced/gated active illumination for multispectral imaging. Pulsed and synced/gated illumination enables automated multispectral fluorescence image acquisition and processing to be conducted in non-dark environments (i.e., outdoors in daylight or indoors with bright artificial lighting, as well as under darkened conditions) due to rapid processing of images.

For the purposes of this disclosure, an "Ambient light image" is a multispectral image acquired in the ambient light present in an inspection space without the presence of active illumination from the light source 56 present on the CSIS 20.

Further, for the purposes of this disclosure, an "Illuminated image" comprises a multispectral image acquired in the ambient light present in an inspection space and with the presence of active illumination from the light source 56 present on the CSIS 20.

System Operation

Pulsed and synced/gated illumination enables processing for immediate, nearly instantaneous fluorescence-based feature detection for real-time inspection of the scene being examined by a user. In the preferred embodiment, real-time highlighting of detection results can be captured "live" on the CSIS screen 32. Alternatively, the detection results can be captured in still images as selected by the user. The results of the inspection can be viewed, processed, and recorded as a continuous video stream, or as a series of still images. In either case, detected contamination is preferably depicted as an image of fluorescence. The inspection data can be communicated via any wireless (BLUETOOTH, wifi, etc.) or wired communication format/means.

Essentially, in accordance with the image acquisition protocol, the CSIS 20 takes two multispectral images under two conditions: the first image (an "Illuminated image") is taken with the selected LED lights 56 pulsed "on" in ambient light conditions; and, the second image (an "Ambient light image") is taken with the LED lights 56 pulsed "off" in ambient light conditions.

The multispectral fluorescence response of objects within the field of view of the camera is acquired through the following equation:

$$\text{Multispectral fluorescent image} = \text{Illuminated image} - \text{Ambient light image}$$

For example, a single multispectral image acquisition protocol (a "single shot" image acquisition cycle triggered by the user) comprises the steps of:

1. Pulse the LED light source 56 ON, (fluorescence excitation) and the CSIS 20 acquires an illuminated image at the two or three filtered targeted wavebands (as shown in FIG. 4).
2. Pulse the light source 56 OFF, and the CSIS 20 simultaneously acquires an ambient light image at the same two or three targeted wavebands under ambient light (background conditions).
3. The CSIS processor 40 software automatically processes the acquired images to subtract the ambient light image from the illuminated image to acquire a multispectral fluorescence image of the inspection area.
4. The CSIS processor 40 software automatically highlights contamination targets within the inspection area and displays the multispectral fluorescence image onscreen 32 for the user, including: (1) image registration to correct slight mismatch of images resulting from any movement of device between the ON and OFF pulsing of the light source 56; (2) background removal; and, (3) band ratios; and (4) multispectral image processing algorithms.

In operation, the "single shot" protocol described in steps 1-4 is repeated continuously until the inspection is complete.

Data Analysis

The image data generated by CSIS 20 can be analyzed using computer vision classification algorithms. The detection algorithm continuously adapts to changing fluorescence and background intensity levels. While imaging with a fixed-mount camera can allow simple conventional thresholding (e.g., Otsu method) and supervised learning, constantly moving the camera across different scenes is more complex. To address this complexity, the inventors adopted adaptive thresholding to change the threshold dynamically over each frame. Whenever intensities between an object's fluorescence and the image background are significant, but their exact magnitude or location in the image is unknown, segmentation is possible by threshold optimization through the image intensity histogram. Alternatively, the image data can be analyzed using deep learning approach to provide semantic segmentation for the precise detection and segmentation of contaminated areas. Over the past ten years, there have been significant contributions to semantic segmentation systems by neural network systems including ALEXNET, GOOGLENET, and RESNET by MICROSOFT. Semantic segmentation assigns classification values at the pixel level in an image.

The CSIS 20 can be also connected to a cloud data base with a distributed learning paradigm (e.g. Federated Learning) that can learn a global or personalized model from decentralized datasets on edge devices (including CSIS). This is highly desirable for the users who do not share a complete data set with the main cloud system due to privacy concerns, while the data analytics (e.g. image classification, image segmentation, and object detection) is highly needed to improve the contamination detection and segmentation learner.

Inspection Protocol

Figure 5:
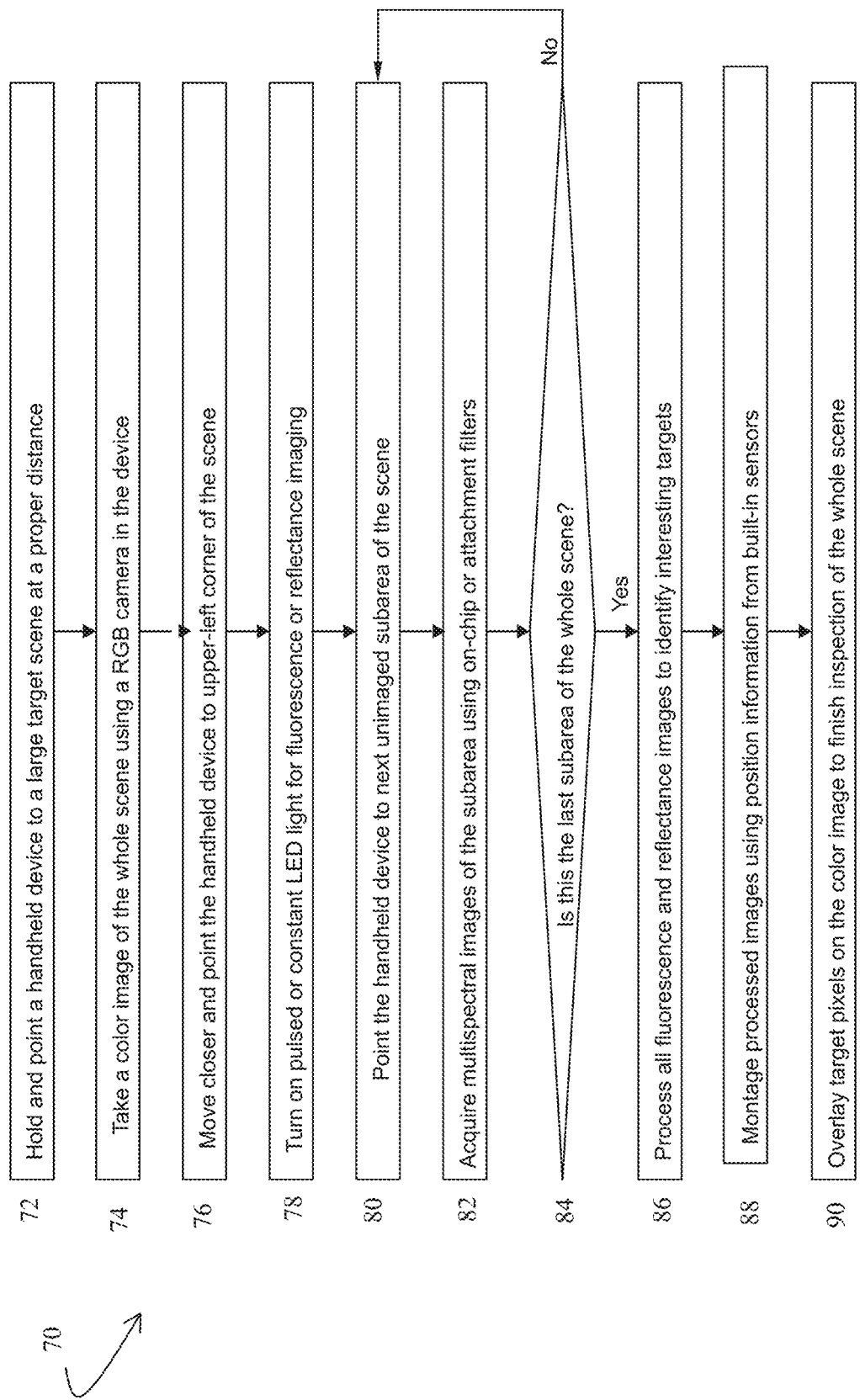
FIG. 5 is an exemplary flowchart of an inspection protocol.

FIG. 5 generally describes the data gathering and processing protocol 70. In accordance with the protocol 70, a user holds and points the CSIS 20 in the direction of an inspection area and takes a color image of the whole scene using the primary multispectral camera 52. As the inspection progresses, the user systematically acquires multispectral images of the entire inspection area (FIG. 5 reference numbers/steps 72-84).

As further described in FIG. 5 reference numbers/steps 86-90, once the area/sub area inspection is complete, the CSIS processor 40 processes all fluorescence and reflectance images to identify any contamination or anomalies and a virtual montage of the inspection area is created and the data is presented as an overlay of the inspection area to allow a user to take remedial action if required. Alternatively, the CSIS processor 40 may process the multispectral images in real time, based on the capability of the processor and/or the needs of the inspector.

Mapping

In the preferred embodiment, the CSIS 20 is equipped with position/orientation sensing hardware (e.g., GPS, accelerometer, motion/rotation sensor, rangefinder, light detecting and ranging (LiDAR) technology, etc.) to create feature maps and to precisely identify features of interest imaged at close range within a larger scene image. In the case of a facility inspection, the location of any detected contamination can be mapped onto a representational map or floorplan (that may also be preloaded). Mapping the position of detected contamination relative to localized reference features within a larger scene provides precise reference data that can make remediation/decontamination more efficient and reliable. The inclusion and mapping of reference features means that users/inspectors no longer have to rely on human observation and memory or descriptive note-taking.

Specific Alternative Embodiments

Although multiple alternative embodiments of the current system 20 are identified in this disclosure, the current section of the disclosure further discusses some specific embodiments. This section is not intended to be a complete list of possible embodiments or to limit the number and type of embodiments in any way.

In one alternative embodiment, the CSIS 20 may incorporate a disinfection means, so that the composite system comprises a sanitation inspection and disinfection system (hereinafter a "CSI-D"). In the CSI-D embodiment, the inspection area-facing side of the CSIS specifically further includes excitation lights 56 comprising UV-B or UV-C active illumination lights, or the excitation lights 56 may comprise other types of electromagnetic radiation or laser lights having disinfecting/sanitizing capabilities. The CSI-D embodiment enables a user to effectively sanitize an inspected surface after the inspection process identifies a contaminating material on the inspected surface.

The CSI-D embodiment also enables a process of multispectral fluorescence inspection and decontamination of live plants in a plant production area/facility such as a farmer's field, a greenhouse, a hydroponics production facility, or any other area where plants are produced. In a plant production environment, the CSI-D is used to detect either (1) the presence/location of plant disease agents such as mildew, fungal spores and mycelia, bacterial/viral infection points, or (2) the symptoms of such diseases, both of which would be detected in fluorescence images of the plant tissues. Inspection with real-time image processing to highlight the contaminant locations or plant symptoms can then be followed immediately by UVB/UVC treatment to (1) deactivate plant disease agents or mitigate the severity of their effects, or (2) strengthen the plant by inducing an increase in UV light-sensitive defenses and by gene activation to stimulate biological defense responses to aid the plant's resistance to or recovery from the disease agents.

In a further alternative embodiment, mobile or portable devices such as smartphones, tablets, laptops, or other devices that may include a camera and/or data processing capabilities may be augmented or modified to perform some of the functions described herein.

Figure 7:
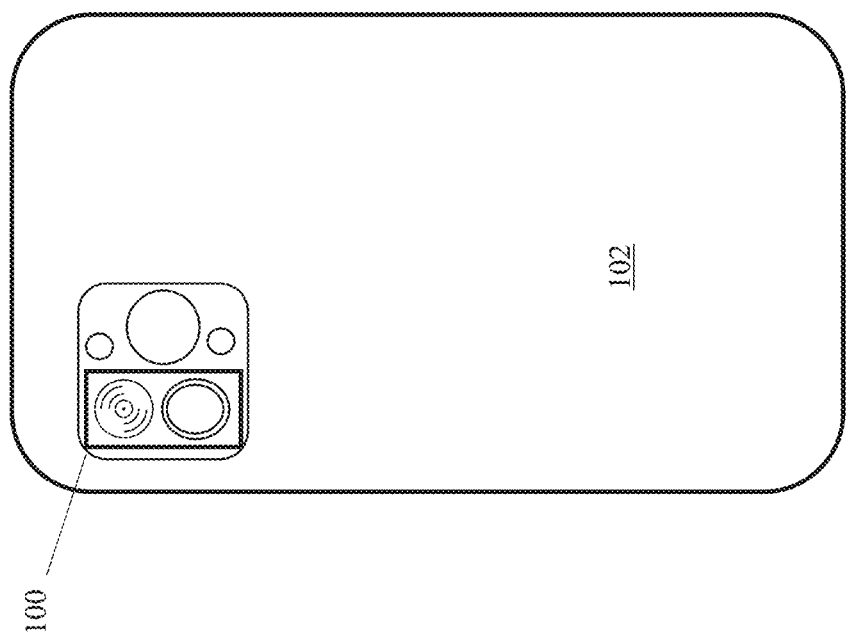
FIG. 7 shows the enhanced cell phone 102 with the CSIS supplemental module 100 installed.
Figure 6:
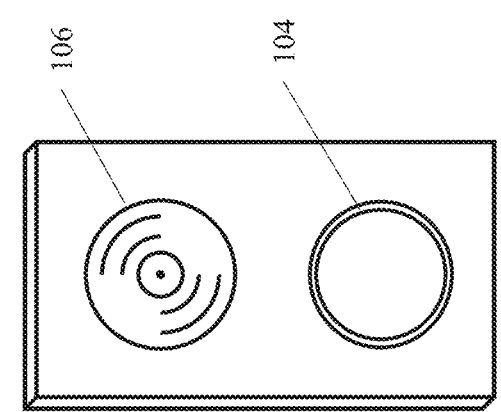
FIG. 6 shows a CSIS supplemental module 100 that can be added to a mobile device, such as a smart phone, to create an enhanced cell phone 102 with at least some CSIS capabilities. Note that it may be possible to modify other multifunctional electronic devices that have (or can be modified to have) a camera to perform some CSIS 20 functions.

As shown in FIGS. 6 and 7, a supplemental camera/active illumination module 100 can be added to a cell phone to create an enhanced cell phone 102 with at least some CSIS-type capabilities. The CSIS supplemental module 100 comprises a camera with a narrow band pass multispectral filter 104 and a user-selectable light source 106. As shown in FIG. 7, the necessary structural modifications to the existing cell phone are relatively minor. Software modifications will be also be required to modify a conventional cell phone to operate with the enhanced CSIS capabilities.

For the foregoing reasons, it is clear that the subject matter described herein provides a compact and innovative multispectral imaging system 20 to be used for surface inspection and contamination identification under a wide range of ambient light conditions. The current system 20 may be modified in multiple ways and applied in various technological applications. For example, the system 20 may be modified to include a decontamination capability. The system 20 may also take the form of a modified cell phone 102 or other modified electronic device. The disclosed method and apparatus may be modified and customized as required by a specific operation or application, and the individual components may be modified and defined, as required, to achieve the desired result.

Although the materials of construction are not described, they may include a variety of compositions consistent with the function described herein. Such variations are not to be regarded as a departure from the spirit and scope of this disclosure, and all such modifications as would be obvious to one skilled in the art are intended to be included within the scope of the following claims.

The amounts, percentages and ranges disclosed in this specification are not meant to be limiting, and increments between the recited amounts, percentages and ranges are specifically envisioned as part of the invention. All ranges and parameters disclosed herein are understood to encompass any and all sub-ranges subsumed therein, and every number between the endpoints. For example, a stated range of "1 to 10" should be considered to include any and all sub-ranges between (and inclusive of) the minimum value of 1 and the maximum value of 10 including all integer values and decimal values; that is, all sub-ranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the implied term "about." If the (stated or implied) term "about" precedes a numerically quantifiable measurement, that measurement is assumed to vary by as much as 10%. Essentially, as used herein, the term "about" refers to a quantity, level, value, or amount that varies by as much 10% to a reference quantity, level, value, or amount. Accordingly, unless otherwise indicated, the numerical properties set forth in the following specification and claims are approximations that may vary depending on the desired properties sought to be obtained in embodiments of the present invention.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The term "consisting essentially of" or excludes additional method (or process) steps or composition components that substantially interfere with the intended activity of the method (or process) or composition, and can be readily determined by those skilled in the art (for example, from a consideration of this specification or practice of the invention disclosed herein). The invention illustratively disclosed herein suitably may be practiced in the absence of any element which is not specifically disclosed herein. The term "an effective amount" as applied to a component or a function excludes trace amounts of the component, or the presence of a component or a function in a form or a way that one of ordinary skill would consider not to have a material effect on an associated product or process.

What is claimed is:

1. A handheld contamination sanitation inspection system (CSIS), the CSIS comprising:
   at least one active illumination light;
   at least one multispectral camera, the camera comprising a chip-based multispectral camera; and,
   a processor controlling the at least one active illumination light and the at least one multispectral camera;
   wherein, the CSIS is structured so that as a user directs the CSIS toward a target inspection area in various ambient light, the illumination light is pulsing with controlled pulse width, the processor directs the at least one multispectral camera synchronized with the pulsed illumination to acquire a multispectral ambient light image of the inspection area, and immediately thereafter the processor pulses the at least one active illumination light, and the at least one multispectral camera simultaneously acquires a multispectral illuminated image of the inspection area, the processor then subtracting the multispectral ambient light image from the multispectral illuminated image to produce a multispectral fluorescence image of the inspection area.

2. The handheld CSIS of claim 1 wherein the chip-based multispectral camera comprises an image sensor so that the surface of the image sensor comprises a matrix of narrow bandpass filters.

3. The handheld CSIS of claim 2 wherein the multispectral image comprises two or three targeted light bands.

4. The handheld CSIS of claim 3 wherein each of the targeted light bands is about 10-30 nm wide.

5. The handheld CSIS of claim 1 wherein the CSIS is structured so that the processor is within a main body of the CSIS.

6. The handheld CSIS of claim 1 wherein the CSIS processor is located remotely from a main body of the CSIS.

7. The handheld CSIS of claim 1 wherein the multispectral fluorescent contamination image is produced in real time.

8. The handheld CSIS of claim 1 wherein the multispectral fluorescent contamination image is produced after all images including with and without illumination light are gathered.

9. The handheld CSIS of claim 1 wherein the CSIS is controlled manually through a touchscreen on the CSIS and/or through various function activation control means.

10. The handheld CSIS of claim 1 wherein the CSIS further comprises position/orientation sensing hardware.

11. The handheld CSIS of claim 10 wherein the CSIS uses the position/orientation sensing hardware to produce the multispectral fluorescence image of the inspection area on a map of the inspection area.

12. The handheld CSIS of claim 1 wherein a map of the inspection area is downloaded before the inspection, the map including significant inspection area features.

13. The handheld CSIS of claim 1 wherein the inspection area comprises a plant production facility/area.

14. The handheld CSIS of claim 1, wherein the at least one multispectral camera alternatively comprises an RGB camera with multiple narrow bandpass filters.

15. The handheld CSIS of claim 1 wherein the at least one active illumination light, comprises multiple active illumination LED lights, the active illumination lights being selected so that the active illumination lights cause contamination to fluoresce.

16. The handheld CSIS of claim 1 further comprising a UV camera.

17. The handheld CSIS of claim 16 wherein the UV camera includes multiple bandpass filters.

18. The handheld CSIS of claim 1 wherein the CSIS is modified to include one or a combination of UV-B and/or UV-C light active illumination lights, or another type of decontamination laser light or mechanism capable of remediating detected contamination.

19. The modified handheld CSIS of claim 18 wherein the modified CSIS comprises software to function in a plant production facility/area and thereby identify plant disease agents such as mildew, fungal spores, bacterial/viral infection points, or symptoms of associated diseases which would be detected in fluorescence images of the plant tissues.

20. The handheld CSIS of claim 1 wherein the at least one active illumination light works in pulsed/gated mode.

21. The handheld CSIS of claim 1 wherein the sensor is optimized under different ambient light levels so that the system is automated to work with various ambient light conditions.

22. A method of using a multispectral camera and electronically connected processor to produce a multispectral image of an inspection area, the method comprising the steps of:
   (a) the processor pulsing an active illumination LED light source ON (fluorescence excitation), the multispectral camera acquiring an illuminated image at the two or three targeted wavebands and communicating the illuminated image to the processor;
   (b) the processor pulsing the active illumination LED light source OFF, and the multispectral camera simultaneously acquiring an ambient light image at the same two or three targeted wavebands in ambient light only under any of a wide variety of ambient light environments, and communicating the ambient light image to the processor, wherein the processor pulsing the active illumination LED light source ON and OFF produces pulsed illumination that is pulsing with controlled pulse width, and wherein the processor directs the multispectral camera synchronized with the pulsed illumination to acquire the illuminated image and the ambient light image of the inspection area;

(c) the processor automatically processing the images to subtract the ambient light image from the illuminated image to acquire a multispectral fluorescence image of the inspection area.

23. A handheld contamination sanitation inspection system (CSIS), the CSIS comprising:

at least one active illumination light;

at least one multispectral camera, the camera comprising a chip-based multispectral camera, the chip-based multispectral camera comprising an image sensor and a matrix of narrow bandpass filters, wherein the matrix of narrow bandpass filters is configured to pass two or three targeted light wavebands to the image sensor and filter out all other light wavebands, and wherein each of the two or three targeted light wavebands has a span of about 10-30 nm; and, a processor controlling the at least one active illumination light and the at least one multispectral camera;

wherein, the CSIS is structured so that as a user directs the CSIS toward a target inspection area in various ambient light, the illumination light is pulsing with controlled pulse width, the processor directs the at least one multispectral camera synchronized with the pulsed illumination to acquire a multispectral ambient light image of the inspection area, and immediately thereafter the processor pulses the at least one active illumination light, and the at least one multispectral camera simultaneously acquires a multispectral illuminated image of the inspection area, the processor then subtracting the multispectral ambient light image from the multispectral illuminated image to produce a multispectral fluorescence image of the inspection area.

24. The handheld CSIS of claim 23 wherein each of the two or three targeted light wavebands has a span of about 20 nm.

25. The handheld CSIS of claim 24 wherein the matrix of narrow bandpass filters is configured to pass three targeted light wavebands to the image sensor and filter out all other light wavebands, and wherein the three targeted light wavebands comprise about 420-440 nm, about 520-540 nm, and about 690-710 nm.

* * * * *